(12) United States Patent
Miller

(10) Patent No.: US 12,137,875 B2
(45) Date of Patent: Nov. 12, 2024

(54) ENDOSCOPIC DEVICE REMOVAL SYSTEM AND METHOD

(71) Applicant: GI SCIENTIFIC, LLC, Arlington, VA (US)

(72) Inventor: Scott Miller, Arlington, VA (US)

(73) Assignee: GI SCIENTIFIC, LLC, Arlington, VA (US)

( * ) Notice: Subject to any disclaimer, the term of this patent is extended or adjusted under 35 U.S.C. 154(b) by 695 days.

(21) Appl. No.: 17/420,424

(22) PCT Filed: Jan. 3, 2020

(86) PCT No.: PCT/US2020/012251
§ 371 (c)(1),
(2) Date: Jul. 2, 2021

(87) PCT Pub. No.: WO2020/142736
PCT Pub. Date: Jul. 9, 2020

(65) Prior Publication Data
US 2022/0079425 A1 Mar. 17, 2022

Related U.S. Application Data

(60) Provisional application No. 62/788,901, filed on Jan. 6, 2019.

(51) Int. Cl.
*A61B 1/00* (2006.01)
(52) U.S. Cl.
CPC ................. *A61B 1/00131* (2013.01)
(58) Field of Classification Search
CPC .................................................. A61B 1/00131
See application file for complete search history.

(56) References Cited

U.S. PATENT DOCUMENTS 9,516,994 B2* 12/2016 Sato ..................... A61B 8/4494
2011/0021881 A1 1/2011 Wenchell et al.
(Continued)

FOREIGN PATENT DOCUMENTS

JP 4195092 B2 12/2008
WO 2010-142662 A1 12/2010

OTHER PUBLICATIONS

Bacho, Cristina DO1; King, Brian MD2; Gentry, Andrew MD3. Get a Grip: A Bench Test to Evaluate Endoscopic Forceps Grip Strength on Self-Expanding Metal Stents (SEMS): 329. American Journal of Gastroenterology 111():p S153, Oct. 2016. (Year: 2016).*
(Continued)

*Primary Examiner* — Lynsey C Eiseman
*Assistant Examiner* — Christopher J Mutchler
(74) *Attorney, Agent, or Firm* — Farber LLC

(57) ABSTRACT

Systems and methods are provided for the non-traumatic removal of a variety of devices placed over, or on, endoscopic instruments or endoscopes. A device removal system includes a removal element for gripping the device having a body with a central portion and adjacent gripping arms movably coupled to the central portion. The system further includes an insertion device coupled to the removal element and an expanding instrument. The insertion device has an elongate shaft configured for advancement into an opening or channel within the device to be removed. The expanding instrument is configured for insertion into the insertion device to expand the shaft of the insertion device and obtain a firmer grip on the device, thereby reducing the local pressure applied to any one portion of the device, which reduces the wear and tear on the instrument and minimizes damage to epoxy joints and other sealed areas.

20 Claims, 4 Drawing Sheets

(56) References Cited

U.S. PATENT DOCUMENTS

| | | | |
|---|---|---|---|
| 2012/0158043 A1* | 6/2012 | Suzuki | A61B 1/00087 606/205 |
| 2017/0022419 A1 | 1/2017 | Chiou | |
| 2018/0010383 A1 | 1/2018 | Tomlinson | |

OTHER PUBLICATIONS

Korean Intellectual Property Office; International Search Report and Written Opinion; PCT/US2020/012251; GI Scientific, LLC; May 1, 2020.

* cited by examiner

ENDOSCOPIC DEVICE REMOVAL SYSTEM AND METHOD

CROSS REFERENCE TO RELATED APPLICATIONS

This application is the National Stage of International Application No. PCT/US2020/012251 filed Jan. 3, 2020, which claims the benefit of U.S. Provisional Application No. 62/788,901, filed Jan. 6, 2019, the entire disclosures of which are incorporated herein by reference for all purposes.

FIELD

The present disclosure systems and methods for removing medical devices, instruments, accessories or components that are placed over, or on, other medical devices, instruments or components, and more particularly, to systems and methods for removing endoscopic devices from medical instruments or endoscopes

BACKGROUND

Recent advances in optical imaging technology have allowed many medical procedures to be performed today in a minimally invasive manner. The evolution of the more sophisticated, flexible scope with advanced visual capabilities has allowed access to regions deep within the human body that could only be achieved before with invasive surgical intervention. This modern day convenience has resulted in an increase in the demand for, as well as the number of, endoscopic, laparoscopic, arthroscopic, ophthalmoscopic, or other remote imaging visualization procedures performed every year in the U.S. While these procedures are relatively safe, they are not without risks.

Endoscopes are medical instruments that are used for the visual examination of the interior of the body, including lumens, a body cavity or various organs like the heart, liver, pancreas, stomach, colon, bladder, reproductive systems and other parts of the body. Typical endoscopes are long and slender, with a lighted optical feature, to allow ease of introduction into the patient as well as visualization in the process. Endoscopes can be used with other medical devices, instruments or components, such as for example, cutting or cauterizing instruments, for treatment in addition to examination of the body cavity or organ. Some of these endoscopic companion devices or components can be placed over, or onto, the endoscope, such as for example, endoscopic caps, endoscopic shields, sheaths, optical couplers, lenses, variceal banding devices, and endoscopic submucosal resection devices, to name a few. These devices further enhance the functionality of the endoscope and/or provide protection from contamination.

Increasing amounts of evidence show that continuous removal of these various devices from endoscopes over time results in the loosening of epoxy joints and other areas that are supposed to remain sealed to avoid contamination from biomatter during an endoscopic procedure, as well as subjecting the endoscopes to unnecessary wear and tear. Failure to maintain these seals results in areas where biomatter can accumulate, making cleaning and reprocessing of the scope or instrument difficult and therefore potentially prone to harboring pathogens that can colonize and lead to dangerous drug resistant infections, as well as increased scope maintenance costs and shorter useful life for the scopes.

Accordingly, it would be desirable to provide an improved system for effective removal of these endoscopic devices from the endoscope or medical instrument.

SUMMARY

The present disclosure addresses a long-standing need for a removal system to make the removal of various endoscopic devices from instruments and endoscopes more precise, predictable and less traumatic to the instrument or the endoscope upon which the device is installed. According to one aspect of the present disclosure, a system for removing a device from an endoscopic instrument includes a removal element for gripping the device and an insertion element coupled to the removal element. The removal element has a body comprising a central portion and first and second gripping arms movably coupled to the central portion for allowing the operator to obtain a firm grip on the device. The insertion device has a projection configured for advancement into an opening within the device. The insertion device provides a firmer grip on the device for the operator. In addition, it allows the operator to apply a force from within the device to facilitate withdrawal of the device from the endoscopic instrument.

In certain embodiments, the projection comprises an elongate shaft configured to pass through the opening into an internal channel of the device. The elongate shaft of the insertion device is preferably collapsible such that at least a portion of the shaft may have a reduced diameter for advancing through the internal channel of the device. This facilitates advancement of the shaft into the device and allows for the shaft to then expand outwards and create a friction fit within the internal channel of the device to provide a firmer grip on the device. This friction fit also allows the user to apply a force from within the device as it is withdrawn. Applying a force from within the device spreads the application of force so that it is applied from the outside of the device (through the gripping arms) and from the inside through the insertion device. This reduces the local pressure applied to any one portion of the device, which results in a more precise and atraumatic removal, thereby reducing the wear and tear on the instrument and minimizing damage to epoxy joints and other sealed areas.

In an exemplary embodiment, the shaft comprises one or more slits extending in a substantially longitudinal direction to allow for the shaft to collapse upon external pressure from the internal channel of the device. This facilitates advancement of the shaft into the device to be removed. In another exemplary embodiment, the shaft includes ridges on at least one portion of its outer surface to enhance the grip between the shaft and the device.

In certain embodiments, the removal system further comprises an expanding instrument configured for insertion into the insertion device. The expanding instrument preferably has at least one portion with a larger diameter than the internal diameter of the insertion device (at least in its collapsed configuration). The expanding instrument expands the shaft of the insertion device against the internal channel of the device to be removed to further increase the friction fit therebetween. In an exemplary embodiment, the expanding instrument comprises an elongate shaft with an enlarged head on a distal end portion of the shaft. The enlarged head serves to expand the shaft of the insertion device as it advances therethrough. In an exemplary embodiment, the expanding instrument terminates in a tapered tip to facilitate advancement of the expanding instrument into the insertion device.

In certain embodiment, the first and second gripping arms are pivotally coupled to the central portion of the removal element and configured to pivot from a substantially parallel orientation relative to the central portion to a transverse or perpendicular orientation. This design allows the operator to pivot the gripping arms against the device. In an exemplary embodiment, the gripping arms further include one or more ridges on their inner surfaces for providing additional grip against the device. The gripping arms may also include finger gripping elements on their outer surfaces to facilitate handling of the gripping arms. In an exemplary embodiment, the finger gripping elements comprise a projection extending laterally outward from each of the gripping arms. The projection may include a curved distal surface (distal being the surface away from the operator) that allows the operator to place his/her fingers against the curved surfaces. The finger gripping elements provide additional leverage for the operator to provide sufficient force to pull the removal element and device away from the endoscopic instrument.

In some embodiments, the device to be removed is selected from the group consisting of endoscopic caps, endoscopic shields, sheaths, optical couplers, lenses, variceal banding devices, and endoscopic submucosal resection devices. For example, the device to be removed may be an endoscopic device, such as an optical coupler or an endoscopic cap, attached to the distal or proximal end portion of an endoscope.

In another aspect of the invention, a method for removing a device from an endoscopic instrument comprises gripping a portion of the device with a removal element, inserting a projection of the removal element into an opening in the device and applying a force to the removal element to withdraw the device from the endoscopic instrument. In certain embodiments, the projection comprises an elongate shaft coupled to the removal element. The elongate shaft is advanced through an internal channel in the device to be removed. In an exemplary embodiment, the elongate shaft is collapsed as it advances into the internal channel to facilitate the insertion of the shaft into the device.

In certain embodiments, the method further comprises expanding at least a portion of the elongate shaft after it has been inserted into the channel or opening of the device. The shaft may be expanded by inserting an expanding instrument through an internal channel in the shaft. The expanding instrument may include an elongate shaft with an enlarged head that serves to expand the insertion device.

In certain embodiments, the method further includes contacting first and second sides of the device with first and second gripping arms of the removal element. The gripping arms may be pivotally coupled to a central portion of the removal element such that the operator pivots the gripping arms into position against the device. The applying step may include gripping the first and second gripping arms against the device and pulling the central portion of the removal element away from the device to remove the device from the endoscopic instrument.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DETAILED DESCRIPTION

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

The present disclosure provides a system that enables the precise, predictable and less traumatic removal of a variety of devices used in endoscopic procedures. The devices that can be removed include, for example, endoscopic caps, endoscopic shields, sheaths, optical couplers, lenses, variceal banding devices, endoscopic submucosal resection devices, balloons and other such devices that can be placed on, within, or over an endoscope or other devices used endoscopically, interventionally or in other procedures where an instrument or other device is inserted in a body. The present disclosure is particularly useful for removing devices from endoscopes, such as optical couplers and conductive optical elements that may be removably coupled to the distal end portion of an endoscope. Optical coupling devices suitable for removal by the systems and methods of the present invention, for example, are described in International Application Nos: PCT/US2016/043371, filed Jul. 21, 2016, PCT/US2016/035566, filed Jun. 2, 2016 and U.S. Pat. No. 8,905,921, the entire disclosures of which are incorporated herein by reference for all purposes.

Figure 1A:
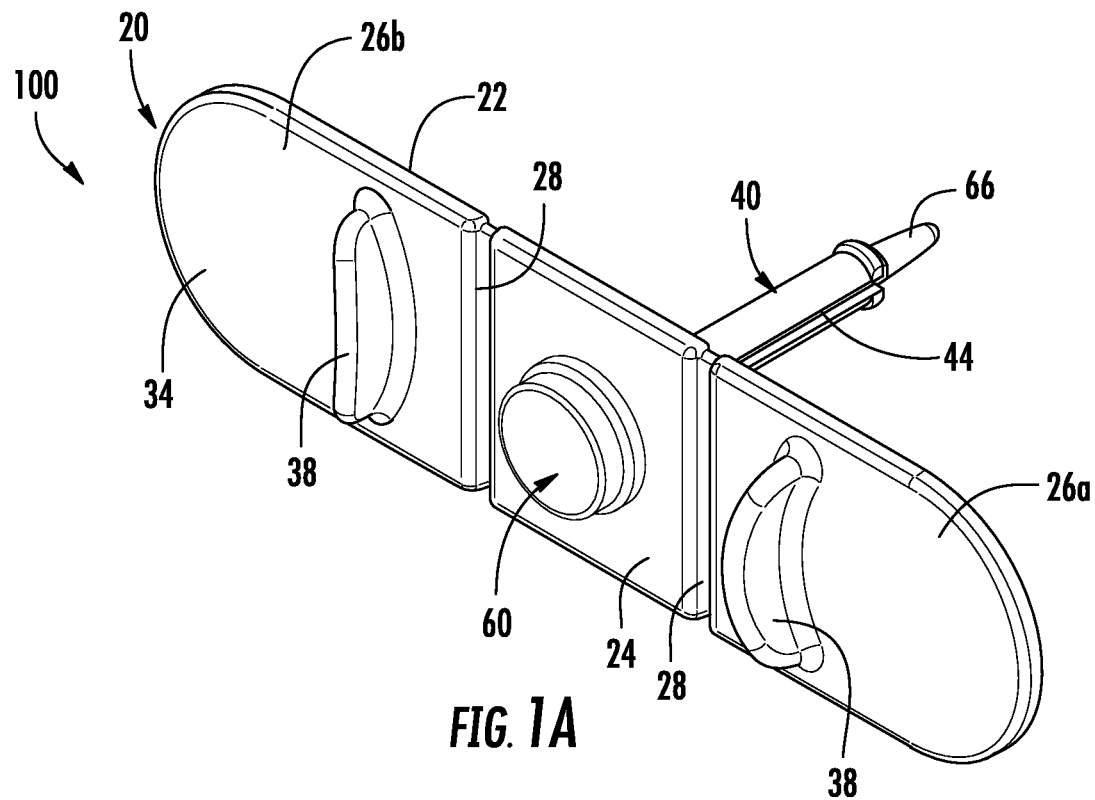
FIG. 1A shows an isometric outer view of a removal system according to the present disclosure in an unfolded configuration.
Figure 1B:
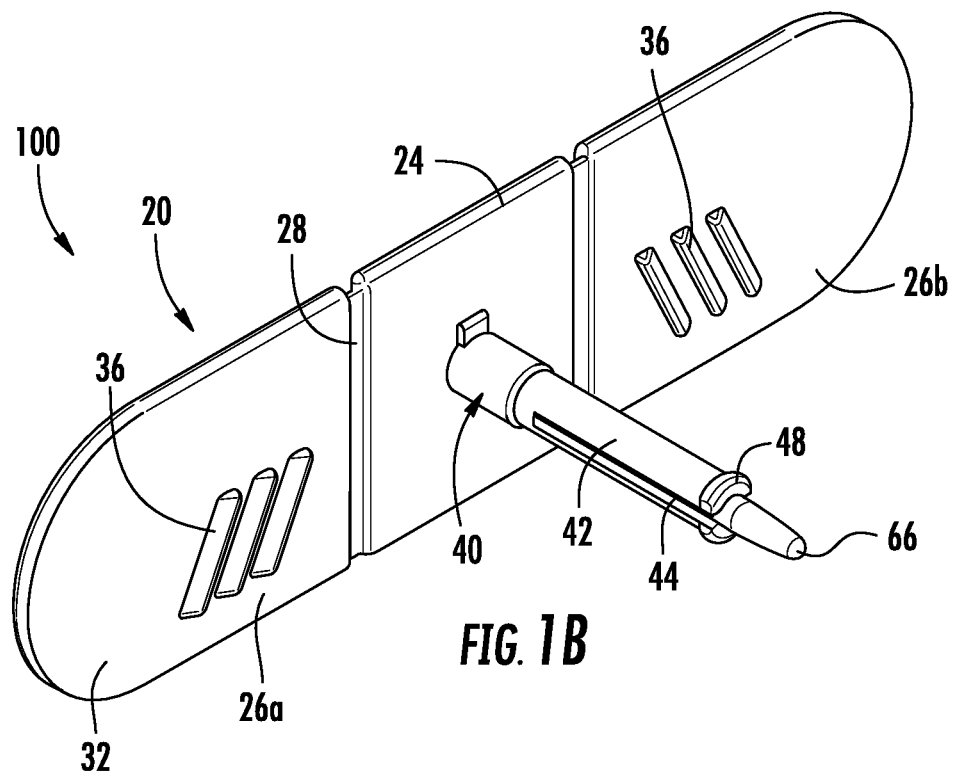
FIG. 1B shows an isometric inner view of the removal system of FIG. 1A.
Figure 1C:
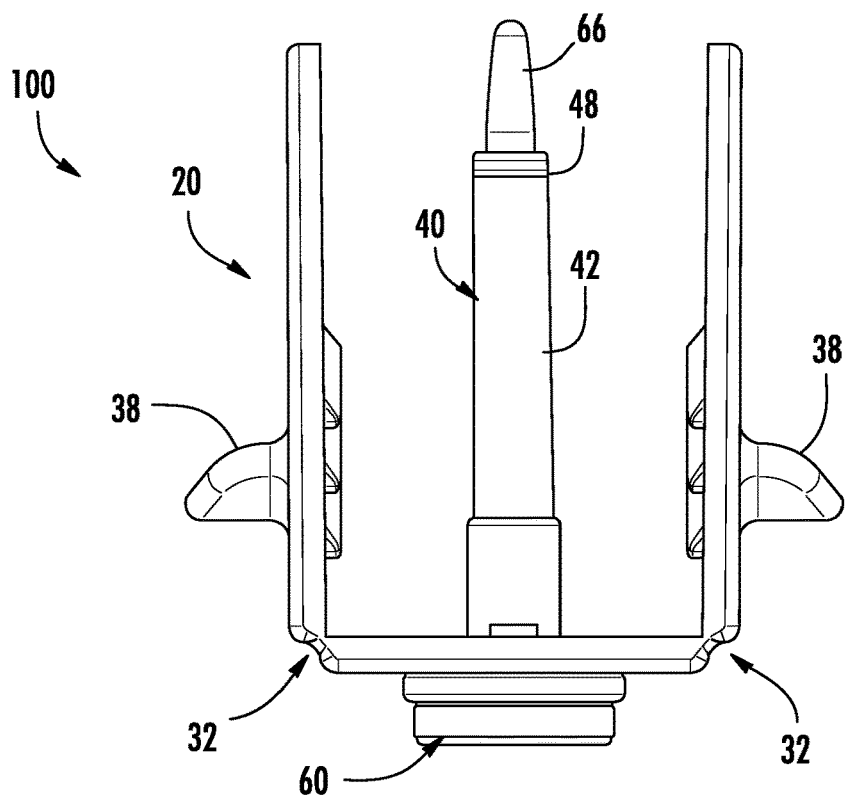
FIG. 1C shows a top-down view of the removal system of FIG. 1A in a folded configuration.
Figure 1D:
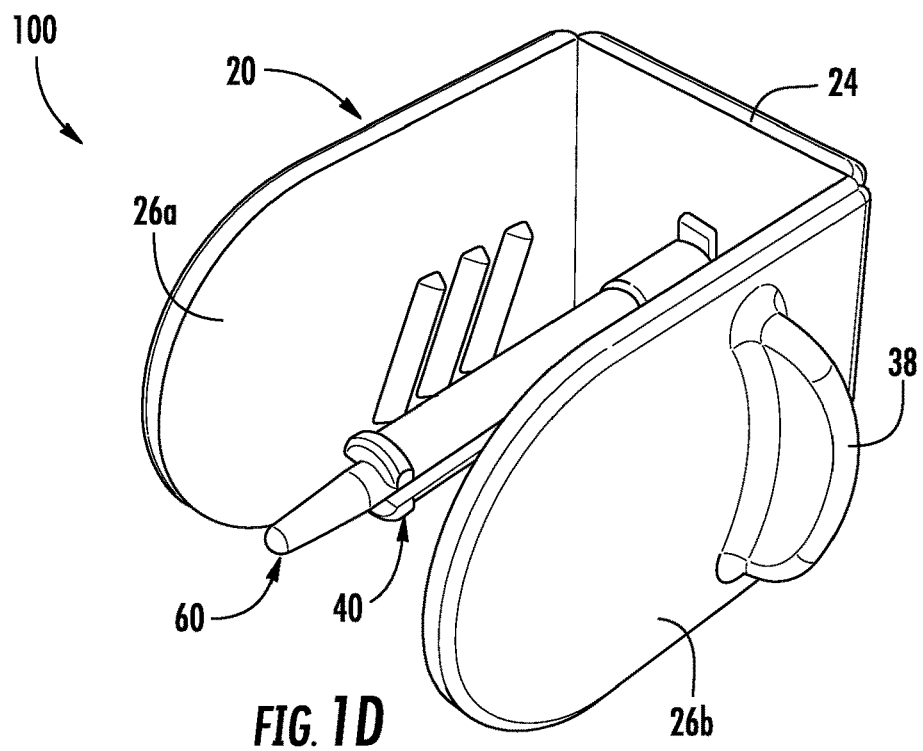
FIG. 1D shows an isometric inner view of the removal system of FIG. 1C.

According to one exemplary embodiment shown in FIGS. 1A-1D, a removal system 100 includes a removal element 20 configured to atraumatically grip and apply force to the outer surface or end of the device being removed, allowing the user to grasp and apply force to the device subject to removal from the endoscope or instrument. The removal element 20 comprises an elongate body 22 having a central portion 24 flanked by adjacent tabs or gripping arms 26a, 26b connected to the central portion 24 at scored areas 28. The scored areas 28 between central portion 24 and gripping arms 26a, 26b enable the gripping arms 26a, 26b to fold or pivot relative to the central portion 24, as shown in FIGS. 1C and 1D. Of course, other configurations are possible. For example, gripping arms 26a, 26b may be pivotally coupled to central portion 24 through a variety of different mechanisms, such as a hinge or other suitable articulation mechanisms.

On the inner surface 32 of the removal element 20, surface protrusions, such as ridges 36 or other suitable gripping elements, can be provided, as shown in FIG. 1B, to increase the grip and application of force to grasp and remove the device subject to removal. The removal element 20 or any other aspect of the system 100 may include finger grip elements 38 on its outer surface 34, as shown in FIG. 1A, to improve the ergonomic aspects of the system by making it easier to hold and apply force to the system 100. In one embodiment, finger grip elements 38 are protrusions extending outwardly from gripping arms 26a, 26b. These protrusions preferably include a curved inner surface configured for contacting the operator's fingers to allow the operator to hold onto grip elements 38 as removal element 20 is being pulled in the proximal direction (or the direction opposite the curved surfaces).

Figure 2:
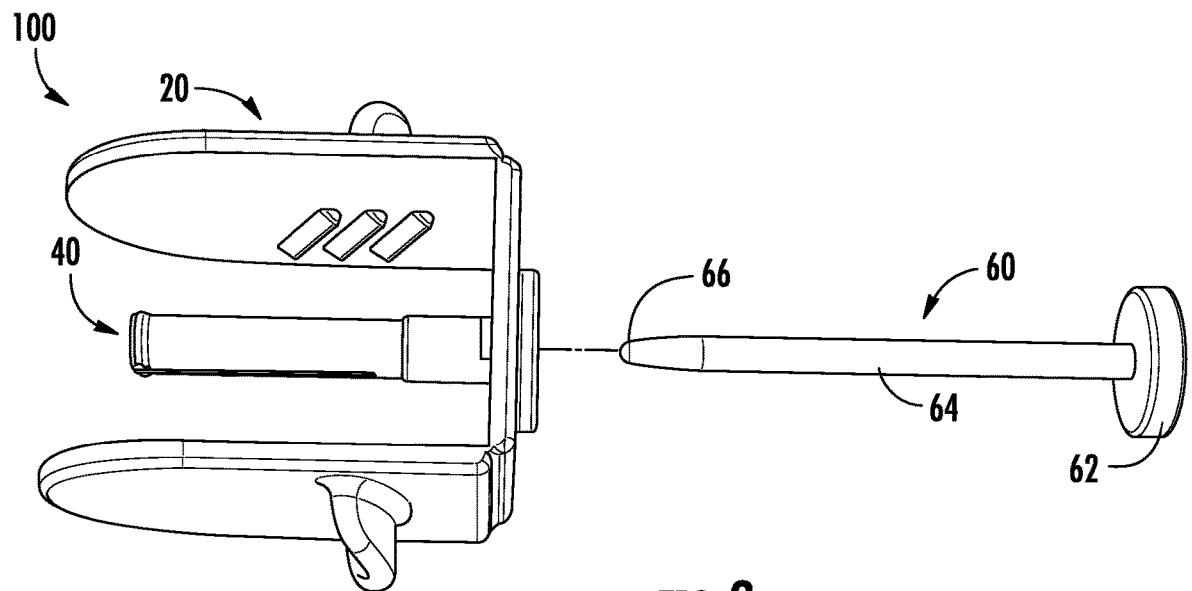
FIG. 2 is an exploded view of the removal system of FIG. 1A.

According to one aspect of the present disclosure, the system 100 may further include an insertion device 40, as shown in FIG. 2, which may be a collet or other suitable element capable of being inserted into the working channel of an endoscopic shield, an optical coupler, an endoscopic cap or other device subject to removal that includes an internal channel. The insertion device 40 may be attachable to the removal element 20, so that the insertion element is advanced into the internal channel of the device subject to removal. Alternatively, insertion device 40 may be an integral part of removal element 20 (i.e., manufactured together in the same mold). The insertion device 40 preferably comprises an elongate shaft 42 with slits 44 or other suitable cutout or design features that allow the insertion device 40 to collapse or otherwise reduce the diameter of its elongate shaft 42 upon insertion. This allows insertion device 40 to be advanced easily through the internal channel of the device subject to removal. In addition, insertion device 40 will then naturally expand outward within the device to create a friction fit between insertion device 40 and the device to be removed. This friction fit allows the user to apply a force from within the device as it is withdrawn. Applying a force from within the device spreads the application of force so that the force being applied is from the outside of the device (through gripping arms 26a, 26b) and from the inside through insertion device 40. This reduces the local pressure applied to any one portion of the device, which results in a more precise and atraumatic removal.

It is of course understood that the removal element 20 may be configured to provide a radial pressure or force from the inside of the device to be removed, or it may be used to spread the ends to capture the device to be removed. In other words, the removal element 20 may be used to effectively grab and pull the device away from the instrument or endoscope on which it is attached by spreading the opening end and pulling the device towards the user.

In alternative embodiments, the insertion device 40 comprises a projection (not shown), such as a knob, flange, lip, extension or other protrusion, that can be inserted into an opening in the device to be removed. In these embodiments, the projection is configured to expand outward upon insertion into the opening to create a friction fit within the device. The projection may, for example, comprise a flexible material that is biased outward by a spring or the natural composition of the material. The user may exert force upon the projection to collapse it and insert it into the opening, whereby it then expands outward to create the friction fit. In one such embodiment, the projection is configured to spread outward upon insertion into the opening such that the projection applies force to the inside proximal surface of the device as it is being withdrawn by the user. In these embodiments, the insertion device 40 may, for example, be used to remove devices that have an opening, but no internal channel therein.

In some embodiments, the insertion device 40 can have one or more ridges 48 or other surface features or variations on its outer surface to increase the amount of adhesion and grip in the internal channel when the removal system 100 is applied to remove the device. Ridges 48 may, for example, be disposed on the outer or distal surfaces of shaft 42.

As shown in FIG. 2, an expanding instrument 60 may be provided for use with the removal system 100. According to another aspect of the exemplary embodiment, insertion device 40 may include an opening 46 (see FIG. 3B) leading into an internal channel (not shown) within elongate shaft 42 for receiving expanding instrument 60. In some embodiments, expanding instrument 60 has a larger outer diameter than the inner diameter of the internal channel of insertion device 40 such that expanding instrument 60 expands insertion device 40. In some cases, the outer diameter of expanding instrument 60 is only larger than the collapsed internal dimeter of insertion device 40 (i.e., after it has been inserted into device and collapsed due to the slits 44 on shaft 42). In other embodiments, the expanding instrument 60 may include an enlarged head portion 62 and an elongate shaft 64 extending from the head portion 62. In these embodiments, the enlarged head portion 62 serves to expand insertion device 40 (i.e., the outer diameter of expanding instrument 60 may be equal to or less than the inner diameter of insertion device 40). In all of these embodiments, advancing insertion device 40 through opening 46 and into the internal channel of insertion device 40 increases the diameter of elongate shaft 42 and therefore the amount of resistance and transfer of force when the insertion device 40 is used to remove the device subject to removal.

The elongate shaft 64 of expanding instrument 60 may terminate in a tip 66. In some embodiments, the tip 66 may be tapered and either blunt or sharp. Tip 66 serves to facilitate advancement of expanding instrument through the internal channel in insertion device 40.

Figure 3A:
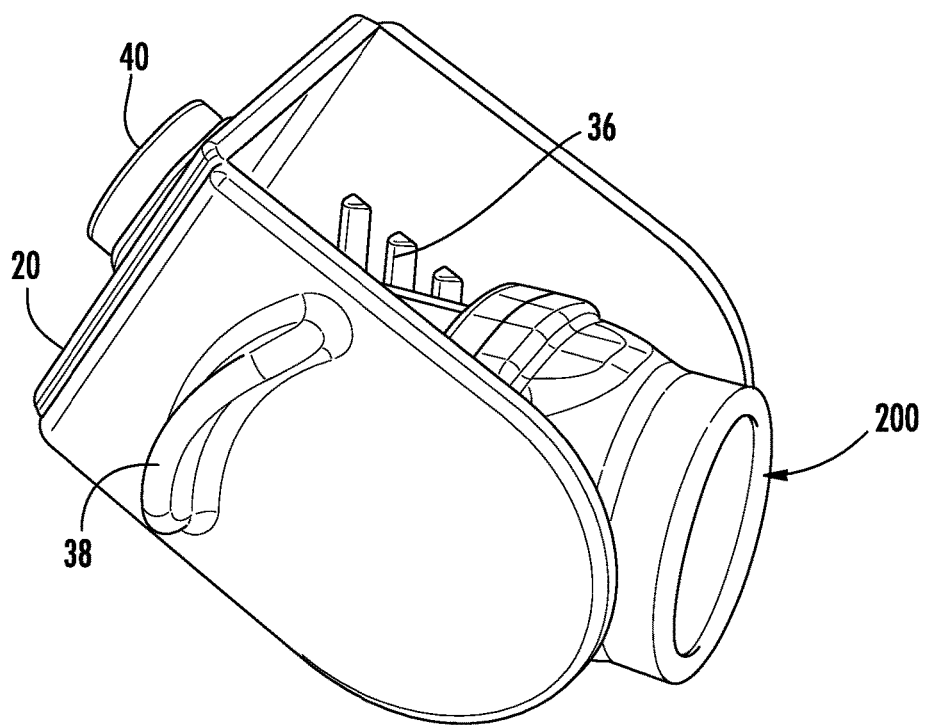
FIG. 3A illustrates a step in a method of removing a device from an endoscopic instrument according to the present disclosure.
Figure 3B:
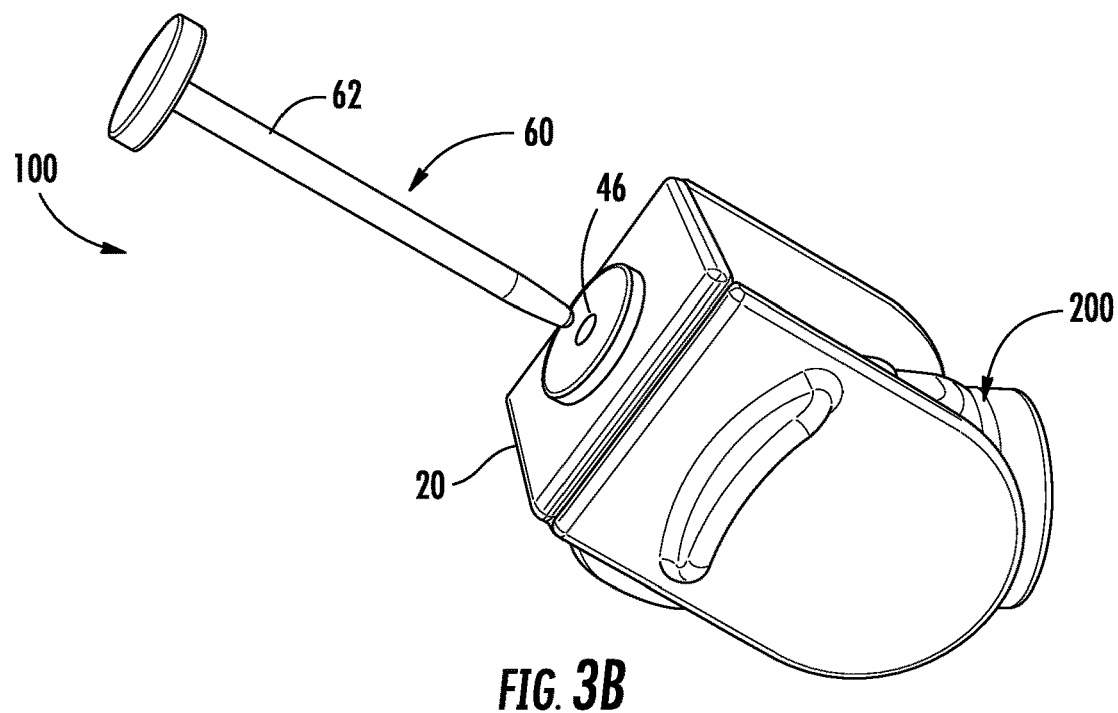
FIG. 3B shows a step of securing the endoscopic device to the removal system by inserting an insertion device.
Figure 3C:
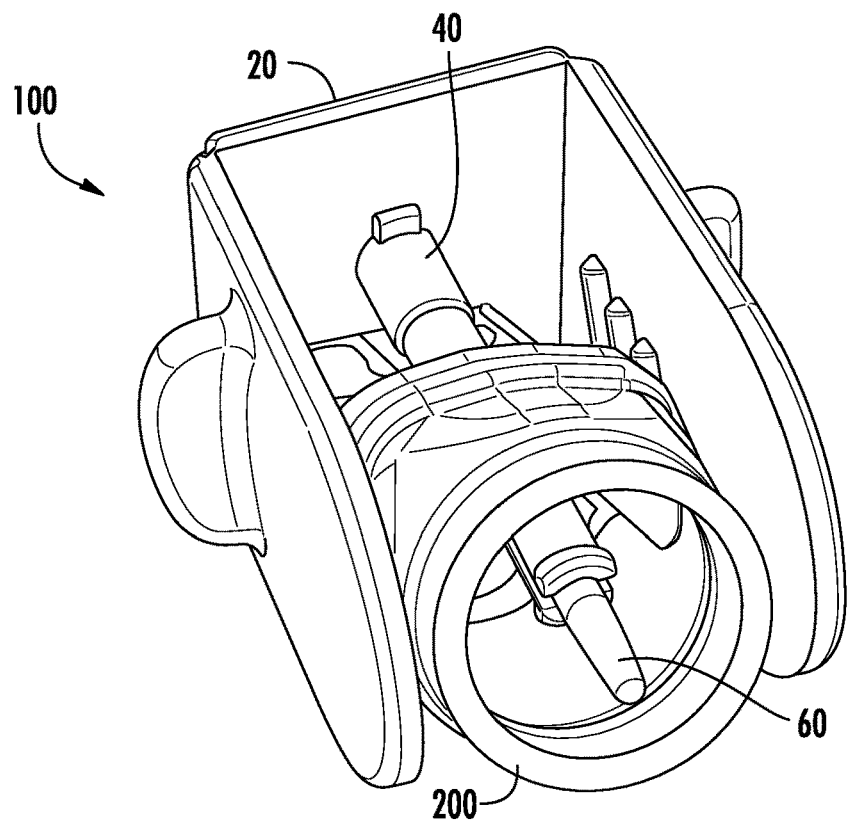
FIG. 3C is an isometric inner view of the removal system and endoscopic device ready to be removed.

Referring now to FIGS. 3A-3C, an exemplary method of removing a representative device 200 that is attached onto an instrument or endoscope according to the present disclosure will now be described. Insertion device 40 is advanced through an opening and into the interior of device, as shown in FIG. 3C. Slits 44 allow shaft 42 of insertion device 40 to collapse to facilitate its advancement through the opening of device 200. The gripping arms 26a, 26b of removal element 20 may then be folded onto the device 200, as shown in FIG. 3A. The ridges 36 on the inner surface 32 of the removal element 20 may allow a secure grip when the user applies pressure using the finger grip elements 38 to fold the removal element 20 over the device 200 to be removed. Next, the expanding instrument 60 may be inserted through opening 46 of the insertion device 60, as shown in FIG. 3B. This expands the diameter of the elongate shaft 42 of the insertion device 40 and further secures the device 200 within the removal system, as shown in FIG. 3C. Once the insertion device 60 has been inserted, the user may grip the entire removal system 100 and pull the device 200 away from the instrument or endoscope, thereby removing the device 200 in a precise, predictable and less traumatic manner than current methods.

The components of the removal system 100 may be made of any medical grade material, including for example, but not by way of limitation, elastomeric materials, rigid materials, combinations of materials to achieve various performance elements that may include both elastic and rigid materials, which may include polypropylenes, PET materials, PTFE materials, thermoplastic elastomers, polycarbonates, acrylics, and any other elastic or rigid medical grade material.

It is of course understood that the removal system 100 may be sterilized using any acceptable method or may be non-sterile. For example, the removal system 100 may be provided as a disposable or single-use system.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A system for removing a device from an endoscopic instrument, the system comprising:
   a removal element for gripping the device, the removal element having a body comprising a central portion and first and second gripping arms movably coupled to the central portion; and
   an insertion device coupled to the removal element and having an elongate shaft configured for advancement into an internal channel within the device, wherein the elongate shaft is collapsible such that an outer diameter of at least a portion of the elongate shaft is reduced upon advancement into the internal channel of the device.

2. The system of claim 1, further comprising an expanding instrument configured for insertion into the insertion device.

3. The system of claim 2, wherein the insertion device comprises an internal open channel for receiving the expanding instrument.

4. The system of claim 2, wherein the insertion device is expandable upon advancement of the expanding instrument into the internal open channel.

5. The system of claim 2, wherein the insertion device comprises slits along the elongate shaft allowing for expansion of the elongate shaft.

6. The system of claim 1, wherein the first and second gripping arms include ridges on an inner surface.

7. The system of claim 1, wherein the first and second gripping arms include finger gripping elements on an outer surface.

8. The system of claim 1, wherein the insertion device includes ridges on the elongate shaft.

9. The system of claim 2, wherein the elongate shaft of the expanding instrument comprises enlarged distal head.

10. The system of claim 9, wherein the elongate shaft of the expanding instrument terminates in a tapered tip.

11. A system for removing a device from an endoscopic instrument, the system comprising:
    a removal element for gripping the device;
    an insertion device coupled to the removal element and having an elongate shaft configured for advancement into an opening within the device; and
    an expanding instrument configured for insertion into the elongate shaft such that the elongate shaft expands within the device, wherein the insertion device comprises slits along the elongate shaft allowing for expansion of the shaft.

12. The system of claim 11, wherein the elongate shaft of the insertion device is collapsible such that an outer diameter of at least a portion of the elongate shaft can be reduced upon advancement into the opening of the device.

13. The system of claim 11, wherein the insertion device comprises an internal open channel for receiving the expanding instrument.

14. The system of claim 11, wherein the removal element includes a body comprising a central portion and first and second gripping arms pivotally coupled to the central portion.

15. The system of claim 13, wherein the elongate shaft of the insertion device is expandable upon advancement of the expanding instrument into the internal open channel.

16. The system of claim 14, wherein the first and second gripping arms include ridges on an inner surface.

17. The system of claim 14, wherein the first and second gripping arms include finger gripping elements on an outer surface.

18. The system of claim 11, wherein the insertion device includes ridges on the projection.

19. The system of claim 11, wherein the elongate shaft of the expanding instrument comprises an enlarged distal head.

20. The system of claim 19, wherein the elongate shaft of the expanding instrument terminates in a tapered tip.

* * * * *